(12) United States Patent
Bernhardt et al.

(10) Patent No.: US 8,952,960 B2
(45) Date of Patent: Feb. 10, 2015

(54) METHOD FOR VISUALIZING AN ATRIUM OF THE HEART IN A PATIENT

(75) Inventors: Dominik Bernhardt, Hausen (DE);
Fernando Vega-Higuera, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 729 days.

(21) Appl. No.: 13/187,575

(22) Filed: Jul. 21, 2011

(65) Prior Publication Data

US 2012/0026169 A1    Feb. 2, 2012

(30) Foreign Application Priority Data

Jul. 29, 2010  (DE) .................. 10 2010 032 755

(51) Int. Cl.
*G06T 15/50*    (2011.01)
*G06K 9/00*    (2006.01)
*A61B 6/00*    (2006.01)

(52) U.S. Cl.
CPC ............... *A61B 6/481* (2013.01); *A61B 6/5217* (2013.01)
USPC ......................................... 345/424; 382/128

(58) Field of Classification Search
CPC ................. A61B 6/5217; A61B 6/481; A61B 2019/463; A61B 2017/00243; A61B 6/504; A61B 5/0456; A61B 5/0422; G06T 19/003; G06T 7/0081; G06T 2207/30048
USPC .......................................... 345/424; 382/131
See application file for complete search history.

(56) References Cited

U.S. PATENT DOCUMENTS

| | | | | |
|---|---|---|---|---|
| 6,443,894 B1 * | 9/2002 | Sumanaweera et al. | ....... | 600/443 |
| 2006/0235294 A1 * | 10/2006 | Florin et al. | .................. | 600/425 |
| 2007/0053553 A1 * | 3/2007 | Gerritsen et al. | ............. | 382/128 |
| 2007/0276225 A1 * | 11/2007 | Kaufman et al. | ............. | 600/416 |
| 2008/0317310 A1 * | 12/2008 | Suresh et al. | ................. | 382/130 |
| 2010/0160768 A1 * | 6/2010 | Marrouche et al. | ........... | 600/420 |

OTHER PUBLICATIONS

Zheng et al., "Four-Chamber Heart Modeling and Automatic Segmentation for 3D Cardiac CT Volumes Using Marginal Space Learning and Steerable Features", IEEE Transactions on Medical Imaging, 27(11), Nov. 2008; Others; 2008.
Tops et al., "Imaging and atrial fibrillation: the role of multimodality imaging in patient evaluation and management of atrial fibrillation", European Heart Journal (2010) 31, 542-551; Others; 2010.
German priority document DE 10 2010 032 755.7 filed Jul. 29, 2010, not yet published.

* cited by examiner

*Primary Examiner* — Kee M Tung
*Assistant Examiner* — Yuehan Wang
(74) *Attorney, Agent, or Firm* — Harness, Dickey & Pierce, P.L.C.

(57) ABSTRACT

In a method for visualizing at least one section of a wall of an atrium of the heart in a patient after an ablation for treatment of atrial fibrillation, a volume data record of at least the treated atrium of the heart in the patient is segmented to establish voxels that are of an inner surface, an outer surface, and a volume situated between the inner and outer surfaces of the wall of the treated atrium. The at least one section of the wall of the treated atrium of the heart is visualized by volume rendering or ray casting such that only voxel values of the established voxels that lie on the inner surface in the volume or on the outer surface of the wall of the treated atrium are used.

17 Claims, 3 Drawing Sheets

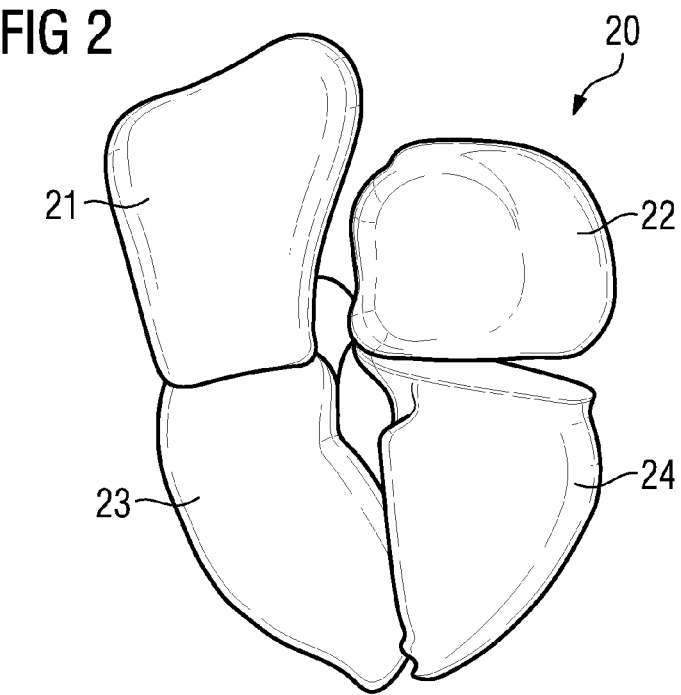
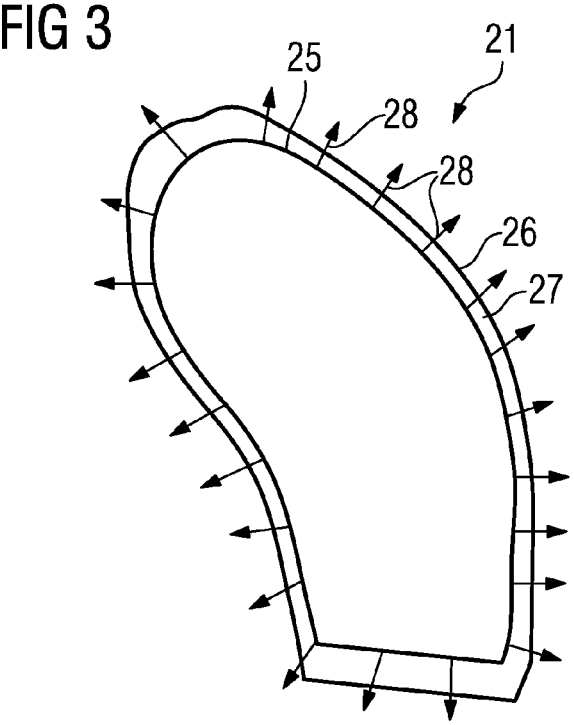

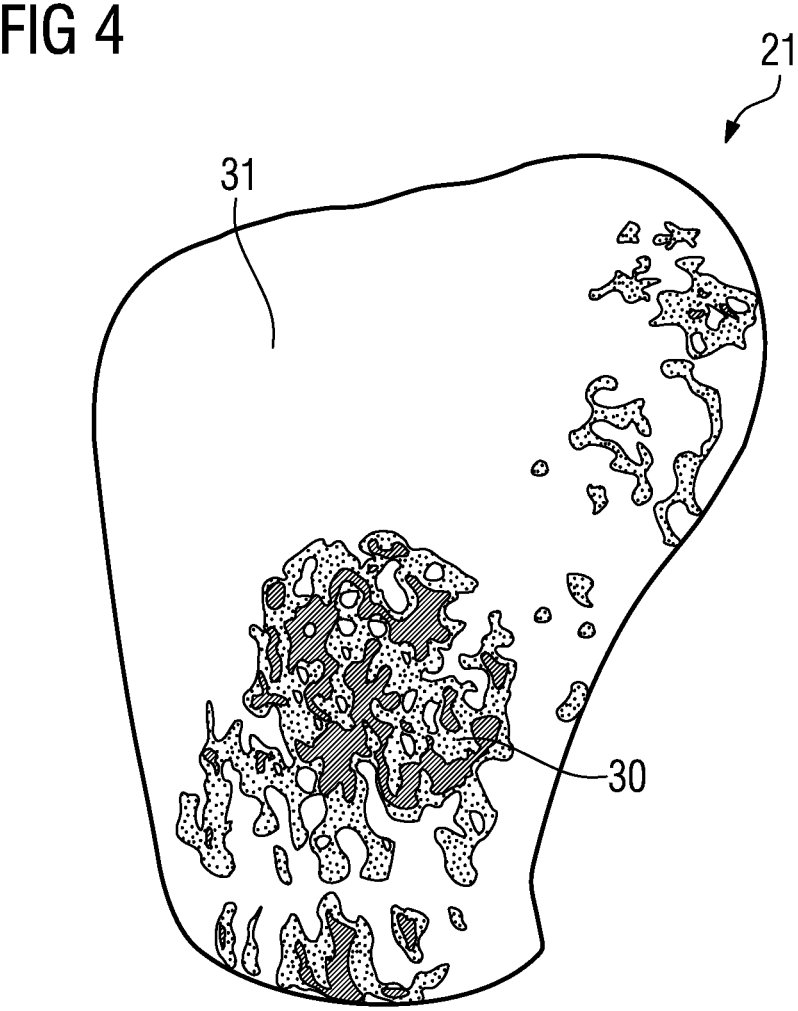

METHOD FOR VISUALIZING AN ATRIUM OF THE HEART IN A PATIENT

PRIORITY STATEMENT

The present application hereby claims priority under 35 U.S.C. §119 on German patent application number DE 10 2010 032 755.7 filed Jul. 29, 2010, the entire contents of which are hereby incorporated herein by reference.

FIELD

At least one embodiment of the invention generally relates to a method for visualizing at least one section of the wall of an atrium of the heart in a patient after an ablation for treating atrial fibrillation in order to be able to assess the result of the ablation. At least one embodiment of the invention moreover relates to a computational program that executes the method, a computational unit that carries out the computational program, and/or a data medium with the computational program.

BACKGROUND

Atrial fibrillation is an arrhythmia, in which there are unordered excitation pulses from the atria to the ventricles in quick succession. As a result of this, the atria and the ventricles contract independently of one another and at different speeds during the atrial fibrillation. The atria and ventricles are normally stimulated approximately 70 times a minute, directly after one another. In the case of atrial fibrillation there are undirected electrical excitations via the atria, which lead to unordered contractions in quick succession with a frequency of between 350 and 600 times per minute. As a result of this high frequency the atria can no longer pump sufficient blood into the ventricles, which likewise pump less blood into the circulatory system, and so there are variations in the blood pressure.

Atrial fibrillation can be treated by medication. If this is unsuccessful, it is increasingly common to carry out a catheter ablation. In the process, a catheter is advanced into the heart via arterial or venous blood vessels. The catheter is used to sever excitation lines running in the tissue of the cardiac wall of an atrium by means of sclerotherapy of tissue in order to suppress the unordered propagation of excitation pulses. In general, either lesions running in the longitudinal direction are placed in the region of the left atrium or muscle bundles at the openings of the pulmonary veins are ablated in an annular fashion.

The treatment success is often monitored with the aid of CT-angiography (CTA), in which, after a contrast agent is administered, an X-ray computed tomography scanner is used to record X-ray projections of the heart in the patient, which are used to reconstruct slice images of the heart in the patient. In this respect, reference is made in an example fashion to Tops L. F., Schalij M. J., and Bax J. J. "Imaging and atrial fibrillation: the role of multimodality imaging in patient evaluation and management of atrial fibrillation", European Heart Journal (2010) 31, p. 542-551.

Particularly if the result of the ablation should be assessed on the basis of image information relating to the treated tissue of the atrium of the heart, it is conventional to generate multiplanar reformations (MPR). However, this procedure for visualizing and representing the treated tissue requires the assessing radiologist to have a high degree of experience and knowledge in the art because the cardiac wall is comparatively thin and the differences between normal, untreated tissue and tissue treated within the scope of the ablation are very small.

SUMMARY

At least one embodiment of the invention is directed to specifying a method, a computational program, a computational unit, and/or a data medium such that conditions are provided so that the assessment of the result of an ablation undertaken on tissue of an atrium of the heart becomes easier.

According to at least one embodiment of the invention, a method is disclosed for visualizing at least one section of the wall of an atrium of the heart in a patient after an ablation for treating atrial fibrillation, in which, based on a volume data record of the heart in the patient obtained after the ablation, at least the treated atrium of the heart in the patient is segmented on the basis of the voxels in the volume data record, wherein those voxels are established that can be considered part of the inner surface, the outer surface, and the volume situated between the inner and outer surfaces of the wall of the treated atrium, and in which there is volume rendering or ray casting such that only the voxel values of those voxels that lie on the inner surface, in the volume, or on the outer surface of the wall of the treated atrium are used for visualizing at least one section of the wall of the treated atrium of the heart.

The treated atrium is generally the left atrium of the heart. The volume data record of the heart in the patient is preferably generated by an X-ray computed tomography scanner within the scope of a CT-angiography (CTA), in which a contrast agent is injected into the patient before the X-ray projections are recorded.

There is a segmentation of at least the treated atrium of the heart on the basis of the generated volume data record. It is preferable for both atria and both ventricles to be segmented. The segmentation makes it possible to determine those voxels that can be considered part of the inner surface, the outer surface, and the volume situated between the inner and outer surfaces of the wall of the treated atrium.

There subsequently is volume rendering or ray casting on the basis of the voxels assigned to the inner surface, the outer surface, and the volume, wherein, for the three-dimensional visualization of at least one section of the wall of the treated atrium or the entire wall of the treated atrium, use is only made of voxels or voxel values assigned to the inner surface, the volume, or the outer surface of the treated atrium. This affords the possibility of generating a comparatively detailed three-dimensional representation of at least one section of the wall of the treated atrium, preferably in an automated fashion and without user interaction, because normal, untreated tissue and tissue treated within the scope of the ablation can be differentiated by mutually deviating voxel values or attenuation values or CT values, and can be visualized accordingly.

The appropriate visualization of treated and untreated tissue provides the conditions for being able to assess the result of an ablation undertaken on tissue of an atrium of the heart in a simpler and faster fashion.

According to one variant of at least one embodiment of the invention, the volume rendering or ray casting is brought about such that beams emanate directed outward from voxels of the inner surface of the treated atrium and/or beams emanate directed inward from voxels of the outer surface, wherein, for the visualization, only the voxel values from those voxels impinged by a beam that lie on the inner surface, in the volume, or on the outer surface of the wall of the treated atrium are used for establishing a beam value. Only one beam preferably emanates per voxel assigned to the inner or outer surface of the wall of the treated atrium, which beam generally impinges on one or more voxels, which are assigned to the wall of the treated atrium, in its beam direction.

The beams, each of which emanates from only one voxel of the inner or outer surface of the wall of the treated atrium, are preferably directed outward orthogonally to the inner surface and/or are directed inward orthogonally to the outer surface. Hence, the beams in each case run in the direction of the normal vector of the respective surface section. The individual surface sections around the voxels assigned to the surface can preferably be set. Since the direction of the normal vector generally changes from surface section to surface section, the beams emanating from the voxels assigned to the surface have a multiplicity of beam directions.

According to a further variant of at least one embodiment of the invention, a beam value is established for each beam by virtue of the fact that the ray casting integral for the respective beam is only calculated within the envelope volume containing the inner surface, the outer surface, and the volume situated between the inner and outer surfaces of the wall of the treated atrium.

According to an alternative, a beam value is established for each beam by establishing a maximum intensity projection for each beam. In the process, the voxel, impinged by the beam, with the maximum voxel value compared to the voxel values of the other voxels impinged by the beam is established for each beam emanating from a voxel of the surface, wherein the voxel value of the voxel from which the beam emanates is also taken into account and which voxel is likewise considered as a voxel impinged by the beam.

One embodiment of the invention provides for the beam value respectively established for a beam is used for visualizing at least the section of the wall of the treated atrium. The beam values of untreated and treated tissue of the treated atrium of the heart will differ from one another irrespective of the procedure used to establish the individual beam values, and so there can be a visualization of untreated and treated tissue on the basis of the beam values.

According to a further embodiment of the invention, there is a color assignment for visualizing at least the section of the wall of the treated atrium, wherein beam values of certain beam-value ranges are assigned specific color values. To this end, beam-value ranges for untreated tissue and beam-value ranges for treated tissue can firstly be set, and color values can subsequently be assigned to these ranges such that there may be a colored visualization of untreated and treated tissue.

According to one variant of at least one embodiment of the invention, at least the treated atrium of the heart in the patient is segmented automatically. Preferably both atria and both ventricles are segmented automatically.

According to a further variant of at least one embodiment of the invention, a model of the heart in the patient is firstly established on the basis of the volume data record of the heart in the patient, with the voxel values of the obtained volume data record being assigned to the model. The segmentation of at least the treated atrium of the heart is preferably brought about on the basis of the model of the heart in the patient. Such modeling and preferably automatic segmentation of the heart can more particularly take place according to the method by Zheng Y., Barbu A., Georgescu M., Scheuering M., and Comaniciu D., described in "Four-Chamber Heart Modeling and Automatic Segmentation for 3D Cardiac CT Volumes Using Marginal Space Learning and Steerable Features", IEEE Transaction on Medical Imaging, November 2008, 27(11), pages 1668-1681, the entire disclosure of which is hereby incorporated herein by reference.

According to one embodiment of the invention, the beam value respectively established for a beam is, for visualizing at least the section of the wall of the treated atrium, projected onto the model such that untreated and treated tissue of the treated atrium of the heart can be visualized on the basis of the model.

At least one embodiment of the present invention is also directed to a computational program, which executes one of the methods described above, and at least one embodiment of the present invention is also directed to a computational unit, which is designed to carry out one of the above-described methods with the computational program. At least one embodiment of the present invention is also directed to a data medium, which has a computational program that executes one of the above-described methods, which computational program is stored on the data medium and can be loaded by a computational unit from the data medium.

BRIEF DESCRIPTION OF THE DRAWINGS

An example embodiment of the invention is illustrated in the attached schematic drawings, in which:

FIG. 2 shows a 3D model of the heart in the patient,

FIG. 3 shows the left atrium of the model of the heart in the patient from FIG. 2, and FIG. 4 shows a visualization of treated and untreated tissue by projecting established beam values onto the left atrium of the model of the heart in the patient from FIG. 2.

DETAILED DESCRIPTION OF THE EXAMPLE EMBODIMENTS

Figure 1:
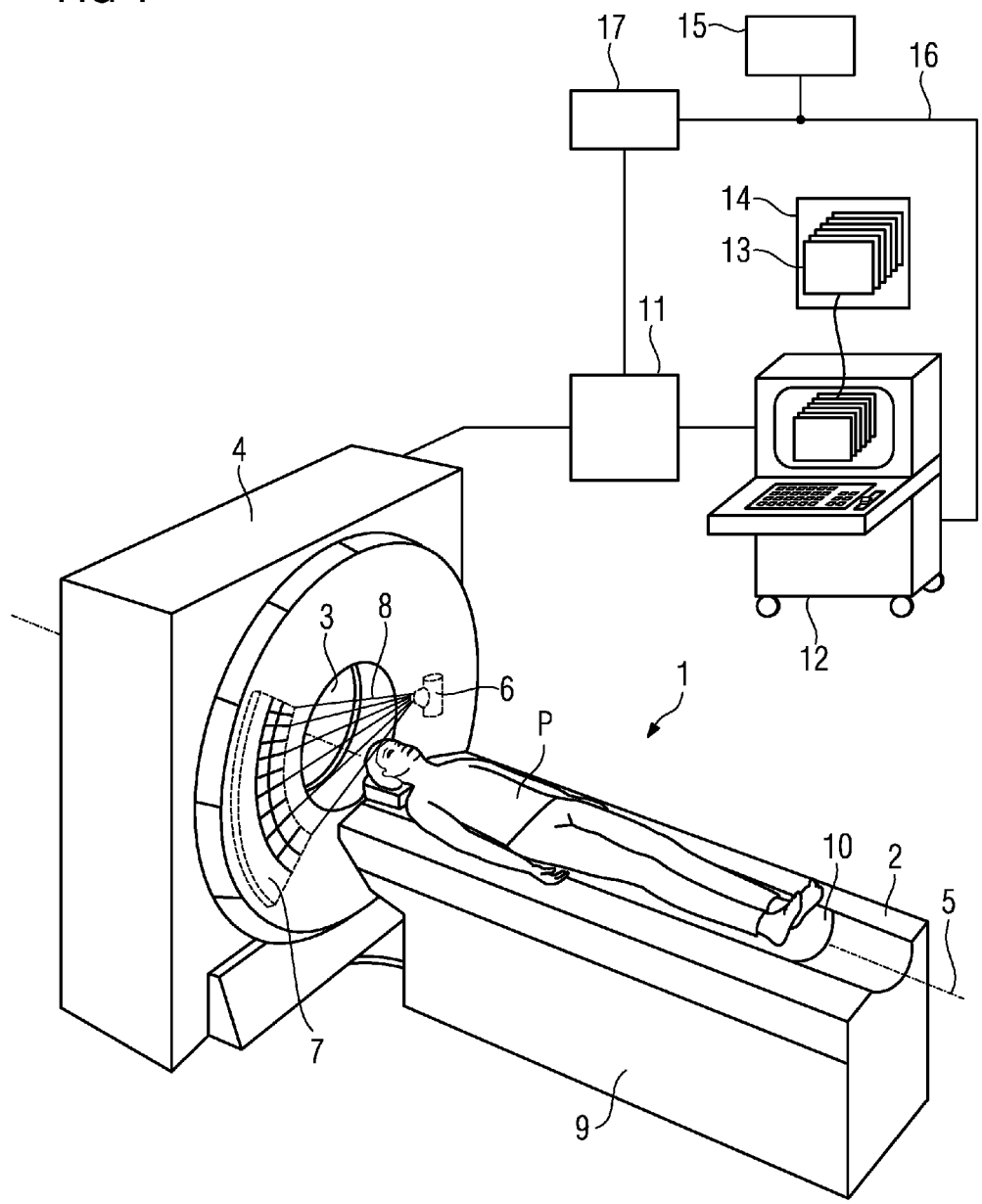
FIG. 1 shows a computed tomography scanner for examining a patient.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, equivalent or functionally equivalent elements, components, tissue, etc. are always provided with the same reference sign. The illustrations in the figures are schematic and not necessarily true to scale, wherein the scales may vary between the figures. The X-ray computed tomography scanner 1 illustrated in FIG. 1 is discussed in the following text and without loss of generality only to the extent considered necessary for understanding the invention.

The computed tomography scanner 1 shown in FIG. 1 has a patient couch 2 for positioning a patient P to be examined. The computed tomography scanner 1 furthermore comprises a gantry 4 with a tube-detector system that is rotatably mounted about a system axis 5. The tube-detector system has an X-ray tube 6 and an X-ray detector unit 7, which lie opposite one another. During operation, X-ray radiation 8 is emitted by the X-ray tube 6 in the direction of the X-ray detector unit 7, and is detected by the latter.

The patient couch 2 has a couch base 9, on which a patient support table 10 provided for actually positioning the patient P is arranged. The patient support table 10 can be adjusted relative to the couch base 9 such that the patient support table 10 with the patient P can be inserted into the opening 3 of the gantry 4 for recording 2D X-ray projections of the patient P, for example in a helical scan. A schematically illustrated image computer 11 of the computed tomography scanner 1 is used for the computational processing of the 2D X-ray projections or the reconstruction of slice images and/or a volume data record of a body region of the patient P on the basis of the 2D X-ray projections.

In the case of the present example embodiment of the invention, the computed tomography scanner 1 is used to examine the heart in the patient P, to be precise after a catheter ablation was carried out in the left atrium of the heart in the patient for treating atrial fibrillation, in order to sever excitation lines running in the cardiac wall of the left atrium by way of sclerotherapy of cardiac tissue and thereby suppress the unordered propagation of excitation pulses. A volume data record obtained in the heart of the patient P should be used, inter alia, to visualize the tissue region treated within the scope of the catheter ablation in order to monitor the treatment success.

In the case of the present example embodiment of the invention, the volume data record is obtained within the scope of a CT-angiography (CTA), in which an e.g. iodine-containing contrast agent is firstly injected into a blood-carrying vessel in the patient P. Using a method known per se, for example within the scope of a helical scan, 2D X-ray projections of the heart in the patient are subsequently recorded from different directions and these projections are used to reconstruct a volume data record of the heart in the patient with the aid of the image computer 11.

In the case of the present example embodiment of the invention, the image computer is connected to a computational unit 12, which is provided for further processing and/or editing of the volume data record. As shown in FIG. 1, the computational unit 12 can be connected directly to the computed tomography scanner 1 for acquiring the volume data record or can access, e.g. via a network 16, a data storage medium 17 of a radiology information system (RIS) or of a hospital information system (HIS), in which the volume data record was stored or saved after being generated by the computed tomography scanner 1 or reconstructed using the image computer 11.

In the case of the present example embodiment of the invention, the computational unit 12 is provided with a computational program 13 that was loaded into the computational unit 12 from a portable data medium 14, which could for example be a CD. However, the computational program 13 could have also been loaded via the network 16 from a server 15, which can also constitute a data medium for the computational program 13. The network 16 need not necessarily only be e.g. a hospital-internal network but can also in part comprise e.g. the Internet or another public network.

The computational program 13, which is executed on the computational unit 12, implements the method for visualizing at least one section of the wall of an atrium of the heart in a patient.

According to one embodiment of the method, a model 20 of the heart in the patient P is firstly generated on the basis of the volume data record generated from the heart in the patient P, with the voxels and voxel values of the volume data record being assigned to this model. The right and left atrium and the right and left ventricle are subsequently segmented automatically on the basis of the model 20 of the heart. The heart in the patient is preferably modeled and the heart is preferably segmented according to the method by Zheng Y., Barbu A., Georgescu M., Scheuering M., and Comaniciu D., described in "Four-Chamber Heart Modeling and Automatic Segmentation for 3D Cardiac CT Volumes Using Marginal Space Learning and Steerable Features", IEEE Transaction on Medical Imaging, November 2008, 27(11), pages 1668-1681, the entire contents of which are hereby incorporated herein by reference. The advantage of this procedure is that both the modeling and the segmentation of the heart can be carried out automatically without user interaction.

FIG. 2 shows the result of modeling and segmentation of the heart in the patient P according to the method by Zheng Y., Barbu A., Georgescu M., Scheuering M., and Comaniciu D., described in "Four-Chamber Heart Modeling and Automatic Segmentation for 3D Cardiac CT Volumes Using Marginal Space Learning and Steerable Features", IEEE Transaction on Medical Imaging, November 2008, 27(11), pages 1668-1681. The left atrium 21, the right atrium 22, the left ventricle 23, and the right ventricle 24 can be identified in FIG. 2.

The left atrium 21, which was treated in the present case and hence is of interest, is once again illustrated in an enlarged fashion in FIG. 3 from a different view, which more particularly illustrates the result of the segmentation of the left atrium 21. FIG. 3 makes it possible to identify that the inner surface 25, the outer surface 26, and the volume 27 between the inner surface 25 and the outer surface 26 of the wall of the left atrium 21 were segmented. In the process, those voxels of the volume data record, on which the segmentation is based, that can be considered part of the inner surface 25, the outer surface 26, and the volume 27 were also established.

Volume rendering, which is understood to be a technique for displaying three-dimensional volume data, or ray casting, which is likewise understood to be a technique for visualizing volumes, is carried out for the visualization, more particularly for the three-dimensional visualization of the wall of the left atrium 21, such that only the voxel values of those voxels that lie on the inner surface 25, in the volume 27, or on the outer surface 26 of the wall of the left atrium 21, which together form an envelope volume, are used for visualizing the wall of the left atrium 21 of the heart in the patient P.

In the case of the present example embodiment of the invention, the volume rendering or the ray casting is carried out such that, as shown in FIG. 3, beams 28 from voxels of the inner surface 25 of the left atrium 21 emanate directed outward orthogonally to the inner surface 26. Here, only one beam 28 emanates per voxel of the inner surface 25, wherein the beam directions of the beams 28 generally differ from one another as a result of the orthogonal arrangement of the beams 28 with respect to the surface. In order to visualize the wall of the left atrium 21, in the end, only the voxel values of those voxels impinged by a beam 28 that lie on the inner surface 25, in the volume 27, or on the outer surface 26 of the wall of the left atrium 21 are used for establishing a resulting beam value.

In the case of the present example embodiment of the invention, a maximum intensity projection is established on the basis of the beams 28, i.e. the voxel, impinged by the respective beam 28, with the maximum voxel value compared to the voxel values of the other voxels impinged by the respective beam 28 is established for each beam 28 emanating from a voxel of the inner surface 25, wherein the voxel value of the voxel from which the respective beam 28 emanates is also taken into account and which voxel is likewise considered as a voxel impinged by the respective beam 28. In the case of the present exemplary embodiment of the invention, the relevant voxel values are attenuation values or CT values. In this fashion, a beam value, which is used for visualizing the wall of the left atrium 21, is established for each beam 28.

In the case of the present example embodiment of the invention, the wall of the left atrium 21 is visualized such that the established beam values of the beams 28 are projected onto the model of the left atrium 21, more particularly onto the inner or outer surface of the model of the left atrium 21. Since the beam values of untreated and treated tissue in the left atrium 21 of the heart 20 in the patient P differ, it is possible to distinguish between treated and untreated tissue sections on the basis of the visualization.

In order to be able to distinguish better between treated and untreated tissue, there additionally is a color assignment in the case of the present example embodiment of the invention for visualizing the wall of the left atrium 21, wherein beam values of specific beam-value ranges are assigned specific color values. In the case of the present example embodiment of the invention, higher beam values, i.e. beam values that embody a relatively high attenuation value, are assigned, in various grades, the colors blue and green. By contrast, comparatively low beam values, i.e. beam values that embody a relatively low attenuation value, are assigned, in various grades, the colors yellow, orange, and red.

This affords the possibility of a colored visualization of untreated and treated tissue of the wall of the left atrium 21, as illustrated in FIG. 4. The tissue regions 30 that can be identified in FIG. 4 are treated tissue, while the tissue regions 31 constitute untreated tissue.

This affords the possibility of immediately distinguishing between treated and untreated tissue, and so, for example, the visualization shown in FIG. 4 can serve as a basis for a radiologist to assess the result of a catheter ablation in the left atrium of the heart in the patient P.

In contrast to the described example embodiment of the invention, the left atrium, the right atrium, and the right and left ventricle of the heart in the patient can also be segmented by other known methods or segmented manually in the volume data of the volume data record such that those voxels are established that can be considered part of the inner surface, the outer surface, and the volume situated between the inner and outer surfaces of the wall of the left atrium.

Moreover, the ray casting integral can be calculated within the envelope volume for each beam 28 instead of the maximum intensity projection such that this also results in a beam value for each beam 28 for visualizing treated and untreated tissue of the left atrium 21, wherein the following holds true for the ray casting integral:

$$I(a, b) = \int_b^a g(s) \exp\left(-\int_a^s \tau(x)dx\right) ds,$$

with
I(a, b) intensity or attenuation value of a voxel,
ds the direction of the associated beam,
g(s) original term of the volume data or intensity function,
τ(x) damping function.

Moreover, the volume rendering or the ray casting can also be carried out such that beams emanate directed inward from voxels of the outer surface, wherein, for the visualization, only the voxel values of those voxels impinged by a beam are used for establishing a beam value that lie on the inner surface, in the volume, or on the outer surface of the wall of the treated atrium.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing at least one section of a wall of an atrium of the heart in a patient after an ablation for treatment of atrial fibrillation and based on a volume data record of the heart in the patient obtained after the ablation, the method comprising:
    segmenting the volume data record of at least the treated atrium of the heart in the patient to establish voxels which are of an inner surface, an outer surface, and a volume situated between the inner and outer surfaces of the wall of the treated atrium; and
    performing volume rendering or ray casting on the at least one section of the wall of the treated atrium of the heart using only voxel values of established voxels lying on the inner surface in the volume or on the outer surface of the wall of the treated atrium, to visualize the at least one section of the wall of the treated atrium of the heart,
    wherein, during the volume rendering or ray casting, at least one of
        beams emanate directed outward from voxels of the inner surface of the treated atrium, and
        beams emanate directed inward from voxels of the outer surface, and
    wherein only the voxel values from the voxels impinged by at least one of the beams and that lie on the inner surface in the volume or on the outer surface of the wall of the treated atrium are used for establishing a beam value.

2. The method as claimed in claim 1, wherein the beams at least one of are directed outward orthogonally to the inner surface and are directed inward orthogonally to the outer surface.

3. The method as claimed in claim 1, wherein the beam value is established for each of the beams by virtue of the fact that the ray casting integral for the respective one of the beams is only calculated within the envelope volume containing the inner surface, the outer surface, and the volume situated between the inner and outer surfaces of the wall of the treated atrium.

4. The method as claimed in claim 1, wherein a beam value is established for each of the beams by establishing a maximum intensity projection for each of the beams.

5. The method as claimed in claim 1, wherein the beam value respectively established for each of the beams is used for visualizing at least the section of the wall of the treated atrium.

6. The method as claimed in claim 1, wherein there is a color assignment for visualizing at least the section of the wall of the treated atrium, and wherein beam values of certain beam-value ranges are assigned specific color values.

7. The method as claimed in claim 1, wherein the treated atrium of the heart in the patient is segmented automatically.

8. The method as claimed in claim 1, wherein a model of the heart in the patient that has the treated atrium is established based on the volume data record of the heart in the patient, and wherein the segmentation of at least the treated atrium is brought about based on the model of the heart in the patient.

9. The method as claimed in claim 8, wherein a beam value respectively established for a beam is, for visualizing at least the section of the wall of the treated atrium, projected onto the model.

10. A non-transitory computer-readable storage medium storing at least one computational program that when executed on a computer device causes the computer device to perform the method as claimed in claim 1.

11. A computer device including a computational unit, designed to implement the method as claimed in claim 1.

12. A non-transitory computer-readable storage medium, including a computational program to perform the method as claimed in claim 1 when executed, the computational program being stored on the non-transitory computer-readable storage medium and being loadable by a computational unit from the non-transitory computer-readable storage medium to carry out the method when the computational program is loaded in the computational unit and executed.

13. The method as claimed in claim 2, wherein the beam value is established for each of the beams by virtue of the fact that the ray casting integral for the respective one of the beams is only calculated within the envelope volume containing the inner surface, the outer surface, and the volume situated between the inner and outer surfaces of the wall of the treated atrium.

14. The method as claimed in claim 2, wherein a beam value is established for each of the beams by establishing a maximum intensity projection for each of the beams.

15. A non-transitory computer readable medium including program segments for, when executed on a computer device, causing the computer device to implement the method of claim 1.

16. The method of claim 1, wherein the volume data record of the treated atrium of the heart is a computed tomography volume data record generated within the scope of a CT-angiography.

17. A method for visualizing at least one section of a wall of an atrium of a heart of a patient after an ablation for treatment of atrial fibrillation, the method comprising:
    segmenting a computed tomography (CT) volume data record of at least the treated atrium of the heart to identify first voxels representing an inner surface of the wall of the treated atrium, second voxels representing an outer surface of the wall of the treated atrium, and third voxels representing a volume between the inner and outer surfaces of the wall of the treated atrium; and
    volume rendering the at least one section of the wall of the treated atrium of the heart using values of only the first and second voxels to visualize the at least one section of the wall of the treated atrium of the heart,
    wherein, during the volume rendering, at least one of
        beams emanate directed outward from the first voxels representing the inner surface of the wall of the treated atrium, and
        beams emanate directed inward from the second voxels representing the outer surface of the wall of the treated atrium, and
    wherein only values from the first and second voxels impinged by at least one of the beams and that lie on the inner surface or on the outer surface are used for establishing a beam value.

* * * * *